(12) United States Patent
Farley (10) Patent No.: US 10,610,408 B2
(45) Date of Patent: Apr. 7, 2020

(54) ILLUMINATED INFUSION CANNULA

(71) Applicant: Novartis AG, Basel (CH)

(72) Inventor: Mark Harrison Farley, Laguna Hills, CA (US)

(73) Assignee: Alcon Inc., Rue Louis-d'affry, Fribourg (CH)

( * ) Notice: Subject to any disclaimer, the term of this patent is extended or adjusted under 35 U.S.C. 154(b) by 0 days.

(21) Appl. No.: 15/987,131

(22) Filed: May 23, 2018

(65) Prior Publication Data

US 2018/0338860 A1    Nov. 29, 2018

Related U.S. Application Data

(60) Provisional application No. 62/510,321, filed on May 24, 2017.

(51) Int. Cl.
| | | |
|---|---|---|
| *A61B 1/07* | (2006.01) | |
| *A61F 9/00* | (2006.01) | |
| *G02B 23/24* | (2006.01) | |
| *A61B 17/34* | (2006.01) | |
| *A61F 9/007* | (2006.01) | |
| *A61B 90/30* | (2016.01) | |
| *A61M 5/158* | (2006.01) | |
| *A61M 39/10* | (2006.01) | |

(52) U.S. Cl.
CPC .............. *A61F 9/0017* (2013.01); *A61B 1/07* (2013.01); *A61B 17/3421* (2013.01); *A61F 9/007* (2013.01); *A61F 9/00736* (2013.01); *G02B 23/2469* (2013.01); *A61B 2017/3433* (2013.01); *A61B 2090/306* (2016.02); *A61M 5/158* (2013.01); *A61M 39/105* (2013.01); *A61M 2207/00* (2013.01)

(58) Field of Classification Search
CPC .... A61F 9/0017; A61F 9/007; A61F 9/00736; A61B 1/07; A61B 17/3421; A61B 2090/306; A61B 2017/3433; G02B 23/2469; A61M 5/158; A61M 39/105; A61M 2207/00
USPC .... 606/2–18, 27, 28; 604/21, 117, 174, 272, 604/294; 600/249
See application file for complete search history.

(56) References Cited

U.S. PATENT DOCUMENTS

| | | | |
|---|---|---|---|
| 4,820,264 A * | 4/1989 | Matsui | ................ A61F 9/00736 604/117 |
| 5,201,730 A | 4/1993 | Easley | |
| 5,275,593 A | 1/1994 | Easley et al. | |
| 5,425,730 A * | 6/1995 | Luloh | ................... A61F 9/0079 604/21 |
| 5,591,160 A | 1/1997 | Reynard | |
| 5,651,783 A | 7/1997 | Raynard | |
| 5,707,368 A * | 1/1998 | Cozean | ................ A61B 18/22 606/15 |

(Continued)

FOREIGN PATENT DOCUMENTS

| | | | |
|---|---|---|---|
| WO | WO2008024848 A2 | 2/2008 | |
| WO | WO2011126812 A1 | 10/2011 | |

*Primary Examiner* — Pedro Philogene (57) ABSTRACT

Systems and methods for assembling an illuminated infusion cannula involving an optical fiber support assembly with an optical fiber support tube and a positioning insert that couples within a cannula and that can position an optical fiber in the tip of the cannula while supporting substantially laminar and minimally-restricted fluid flow through the cannula.

17 Claims, 11 Drawing Sheets

(56) References Cited

U.S. PATENT DOCUMENTS

| | | | |
|---|---|---|---|
| 6,402,734 B1 * | 6/2002 | Weiss | A61F 9/0017 |
| | | | 604/264 |
| 7,783,346 B2 | 8/2010 | Smith et al. | |
| 8,968,347 B2 | 3/2015 | McCollam | |
| 9,055,885 B2 | 6/2015 | Horvath | |
| 9,089,364 B2 | 7/2015 | Bhadri | |
| 9,364,982 B2 | 6/2016 | Schaller | |
| 9,402,643 B2 | 8/2016 | Auld | |
| 9,561,085 B2 | 2/2017 | Yadlowsky | |
| 9,839,749 B2 | 12/2017 | Johnson | |
| 9,956,053 B2 | 5/2018 | Diao | |
| 10,016,248 B2 | 7/2018 | Mirsepassi | |
| 10,039,669 B2 | 8/2018 | Heeren | |
| 2006/0089526 A1 | 4/2006 | Chen | |
| 2009/0161384 A1 | 6/2009 | Smith | |
| 2011/0282160 A1 | 11/2011 | Bhadri | |
| 2014/0121469 A1 | 5/2014 | Meckel | |
| 2017/0014023 A1 | 1/2017 | Kern | |
| 2017/0014267 A1 | 1/2017 | Kern | |
| 2017/0119491 A1 | 5/2017 | Mirsepassi | |
| 2017/0165114 A1 | 6/2017 | Hallen | |
| 2018/0055596 A1 | 3/2018 | Johnson | |
| 2018/0132963 A1 | 5/2018 | Diao | |
| 2018/0133057 A1 | 5/2018 | Diao | |
| 2018/0168768 A1 | 6/2018 | Mirsepassi | |
| 2018/0168861 A1 | 6/2018 | Mirsepassi | |
| 2018/0338776 A1 | 11/2018 | Farley | |
| 2018/0338859 A1 | 11/2018 | Mirsepassi | |

\* cited by examiner

ILLUMINATED INFUSION CANNULA

BACKGROUND

Field of the Disclosure

The present disclosure relates to ophthalmic surgical devices. More specifically, the present disclosure relates to an illuminated infusion cannula.

Description of Related Art

In many ophthalmic procedures a surgeon is required to use a variety of instruments in the patient's eye. Repeated insertion and removal of these instruments can cause trauma to the eye at the incision sites. In an effort to reduce the trauma, a hubbed entry cannula can be used. The hubbed entry cannula can involve a narrow tube with an attached hub. The tube can be inserted into the eye with the attached hub being remaining on the outside of the eye and the hub can have an entry point to allow access to the tube and the interior of the eye.

Although the use of a hubbed entry cannula can reduce repeated trauma, common ophthalmic surgeries oftentimes require insertion of more than one surgical instrument at the same times. For example, common vitreoretinal procedures require a variety of hubbed entry cannulae for the simultaneous use of a handpiece with a vitreous cutter probe, an infusion line for providing irrigating fluid in the eye to maintain intraocular pressure of the eye, an illumination line for illumination of an interior region of the eye, and microsurgical forceps for manipulating tissue.

Other attempts have been made to reduce the amount of incisions, and therefore hubs, required to perform ophthalmic surgeries, e.g. an infusion cannula for insertion into a hubbed cannula with the cannula having an optical fiber coupled to the outer surface of the cannula tip. In this example, the illuminated infusion cannula can be inserted through a hubbed cannula that is previously inserted into an eye. However, this type of illuminated infusion cannula can create shadows in the interior region of the eye that is desired to be illuminated due to the cannula tip partially obscuring the light. Furthermore, the integrity of the optical fiber can be compromised due to interference with the inside wall of the hubbed cannula.

SUMMARY

The disclosed embodiments of the present technology relate to ophthalmic surgical assemblies. Some embodiments of the disclosed technology relate to an optical fiber support assembly used in an illuminated infusion cannula. The optical fiber support assembly can include an optical fiber support tube that couples with an attachment tube and a positioning insert. The attachment tube can couple with an optical fiber illumination assembly and can support a thin optical fiber coming from the optical fiber illumination assembly. The positioning insert can fit into a cannula and can have a passage to hold the optical fiber support tube and the optical fiber and can position the optical fiber in the tip of the cannula.

The positioning insert can also be configured to be arranged in the cannula to allow infusion fluid to flow through the cannula with a substantially laminar flow and minimal restriction. In some cases, the positioning insert is configured with two sets of three arms protruding from the positioning insert. The two sets of three arms can each be configured to contact an inner surface of the flared proximal body of the cannula. The two sets of three arms can also have respective attachment points on opposing ends of the axial length of the positioning insert and can extend away from the respective attachment points and towards the opposing side of the axial length of the positioning insert. The two sets of arms can also include two sets of three arms, can be interleaved, and each of the three arms can be disposed relatively sixty degrees from each other.

In some cases, an ophthalmic surgical assembly includes a Y-shaped fitting with a hollow body and a number of attachment points. The Y-shaped fitting can couple with the optical fiber illumination assembly at a first attachment point and an infusion fluid outlet tube at a second attachment point which is substantially co-axial with the first attachment point. The optical fiber illumination assembly can be aligned with the first attachment point and the optical fiber can be inserted through the first attachment point, the hollow body of the Y-fitting, and the second attachment point. The optical fiber can also be inserted through an infusion fluid outlet tube and the infusion fluid outlet tube can be coupled with the second attachment point of the Y-fitting.

The optical fiber can be threaded into the optical fiber support tube and through the positioning insert. In some cases, the passage in the positioning insert has a decreased diameter portion in a distal end of the passage that resists axial motion of the optical fiber support tube and to allow passage of the optical fiber. The optical fiber extending from the passage of the positioning insert can be threaded into a thin distal tip of the cannula and the can positioning insert can be fit into a flared body portion of the cannula.

The optical fiber support assembly can be slid into the infusion fluid outlet tube and the attachment tube can traverse an opening in the second attachment point, the hollow body of the Y-fitting, and an opening in the first attachment point. The attachment tube can be coupled with an outside portion of the opening in the first attachment point and the optical fiber illumination assembly can also be coupled with the first attachment point to effectively couple the optical fiber illumination assembly with the optical fiber support assembly.

In some cases, when the attachment tube is slid through the first attachment point of the Y-shaped fitting, the cannula is coupled into a distal end of the infusion outlet tube. The distal end of the infusion outlet tube can be elastic and can provides a resisting force on the cannula. The distal end of the infusion outlet tube can also be flared to facilitate the cannula being inserted therein.

The length of the components in an ophthalmic surgical assembly can be selected to select the placement of a distal tip of the optical fiber within the distal tip of a cannula. In some cases, a length of the attachment tube, a length of the optical fiber support tube, and a length of the optical fiber are selected to place the distal fiber tip to a point short of the terminal end of the distal tip of the cannula and where light emitted by the distal fiber tip can spread in a cone through the distal tip of the cannula. The configuration of the distal tip of the optical fiber short of the terminal end of the thin cannula tip can ensure illumination quality while also protecting the optical fiber during insertion through the hubbed entry cannula.

In some cases, the ophthalmic surgical assemblies further include an infusion inlet tube that couples with the third attachment point of the Y-shaped fitting. The infusion inlet tube can deliver infusion fluid through the hollow body of the Y-shaped fitting, over the attachment tube, over the optical fiber support tube, over the positioning insert in the cannula, and out of the thin distal tip of the cannula. The illuminated infusion surgical assembly supports combined illumination and infusion fluid delivery to the eye.

The disclosed embodiments of the present technology also relate to methods of assembling an illuminated infusion cannula. In some cases, a method of assembling an optical fiber support assembly includes coupling a proximal end of an optical fiber support tube into a distal end of an attachment tube and coupling a positioning insert with the distal end of the optical fiber support tube.

The positioning insert can have a passage disposed through an axial length of the positioning insert for accepting the optical fiber support tube. The passage can also include a decreased diameter portion that prevents further axial movement of the optical fiber support tube, but allows for an optical fiber to pass through the decreased diameter portion. Also, assembling an optical fiber support assembly can include coupling the positioning insert into a flared proximal body of a cannula. The passage and the decreased diameter portion of the passage can align with a thin distal tip of the cannula.

The disclosed technology can also involve coupling an infusion fluid outlet tube onto a Y-shaped fitting having a hollow body, a first attachment point for coupling with an optical fiber illumination assembly, a second attachment point for coupling with the infusion fluid outlet tube, and a third attachment point for coupling with an infusion fluid inlet tube, wherein the first attachment point and the second attachment point are configured substantially coaxially. After the infusion fluid outlet tube is coupled to the Y-shaped fitting an optical fiber illumination assembly can be aligned coaxially with the infusion fluid outlet tube and an optical fiber of the optical fiber illumination assembly can be thread through the first attachment point, the hollow body, the second attachment point, and the infusion fluid outlet tube.

Method of assembling an illuminated infusion cannula can also involve sliding the attachment tube of the optical fiber support assembly around the optical fiber, into the infusion fluid outlet tube, through the second attachment point, through the hollow body, through the first attachment point, and into the optical fiber illumination assembly. Further, the methods can involve threading the distal tip of optical fiber into a thin distal tip of a cannula, housing the positioning insert within a flared proximal body of the cannula, and sliding the cannula into a distal end of the infusion fluid outlet tube.

In some cases, an infusion fluid inlet tube is coupled with the third attachment point of the Y-shaped fitting. Illumination from the optical fiber illumination assembly can be delivered through optical fiber and through the cannula at the same time infusion fluid is delivered through the cannula with a substantially laminar and minimally-restricted flow.

BRIEF DESCRIPTION OF THE DRAWINGS

For a more complete understanding of the present technology, its features, and its advantages, reference is made to the following description, taken in conjunction with the accompanying drawings, in which.

DESCRIPTION

The technology described below involves assemblies for illumination infusion cannulas that support an optical fiber and that do not unnecessarily interfere with infusion fluidics and also involves methods for assembling the same.

Figure 1:
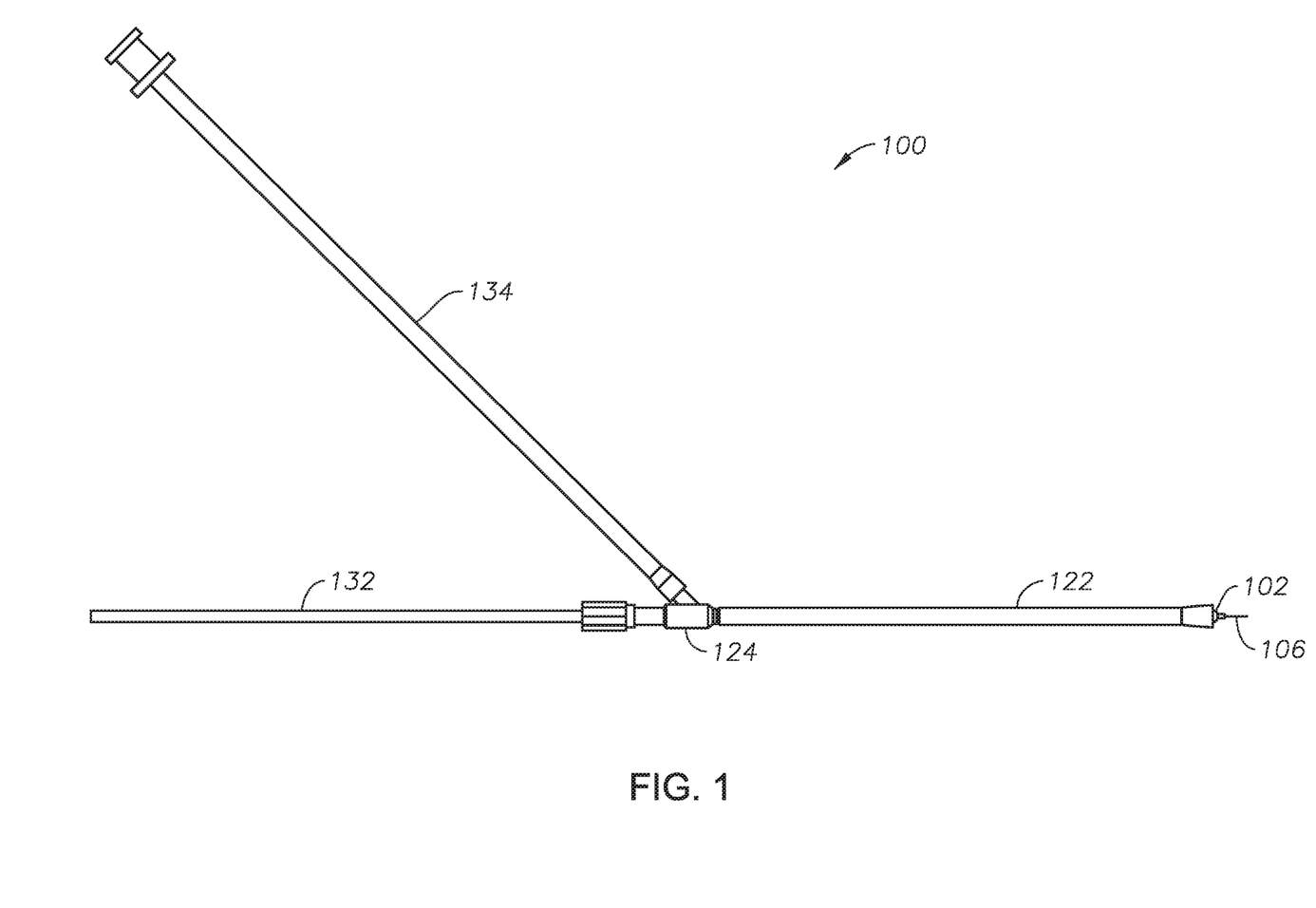
FIG. 1 illustrates an illuminated infusion surgical assembly.

FIG. 1 illustrates an illuminated infusion surgical assembly 100 including an illuminated infusion cannula 102. The illuminated infusion surgical assembly 100 involves an optical fiber illumination assembly 132 and an infusion fluid inlet tube 134 attached to a Y-shaped fitting 124. The illuminated infusion surgical assembly 100 also includes an infusion fluid outlet tube 122 exiting the Y-shaped fitting 124, with the infusion fluid outlet tube containing an optical fiber support assembly (not shown) including an optical fiber (not shown). The infusion fluid outlet tube 122 is coupled with a cannula 102 and the optical fiber (not shown) extends into the distal tip 106 of the cannula. The illuminated infusion surgical assembly 100 can be used for simultaneously delivering infusion fluid through the cannula 102 and providing illumination through the distal tip 106 of the cannula 102.

As explained above, other attempts for providing a combination illumination and infusion cannula have involved placing an optical fiber on the outer surface of the cannula. However, this configuration leads to the optical fiber interfering with the hubbed entry cannula and risks damaging the integrity of the optical fiber. Accordingly, the presently disclosed technology involves an optical fiber support assembly that places the optical fiber inside an infusion fluid outlet tube and inside the interior of a cannula. The optical fiber support assembly is also configured allow substantially laminar and minimally-restricted fluid flow over the optical fiber support assembly.

Figure 2A:
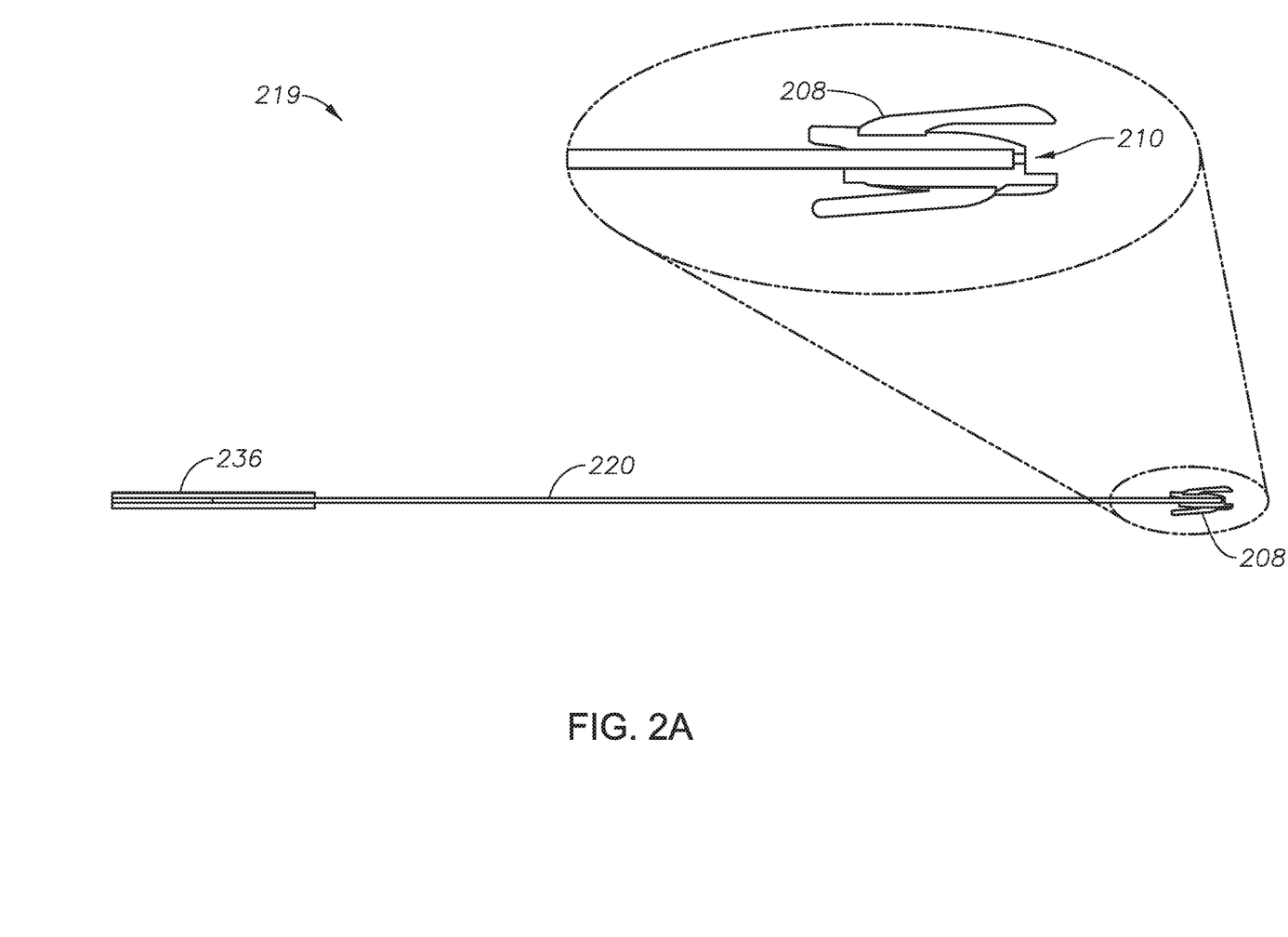
FIG. 2A illustrates the optical fiber support assembly including attachment tube and an optical fiber support tube with a distal end inserted in a passage of a positioning insert.
Figure 2B:
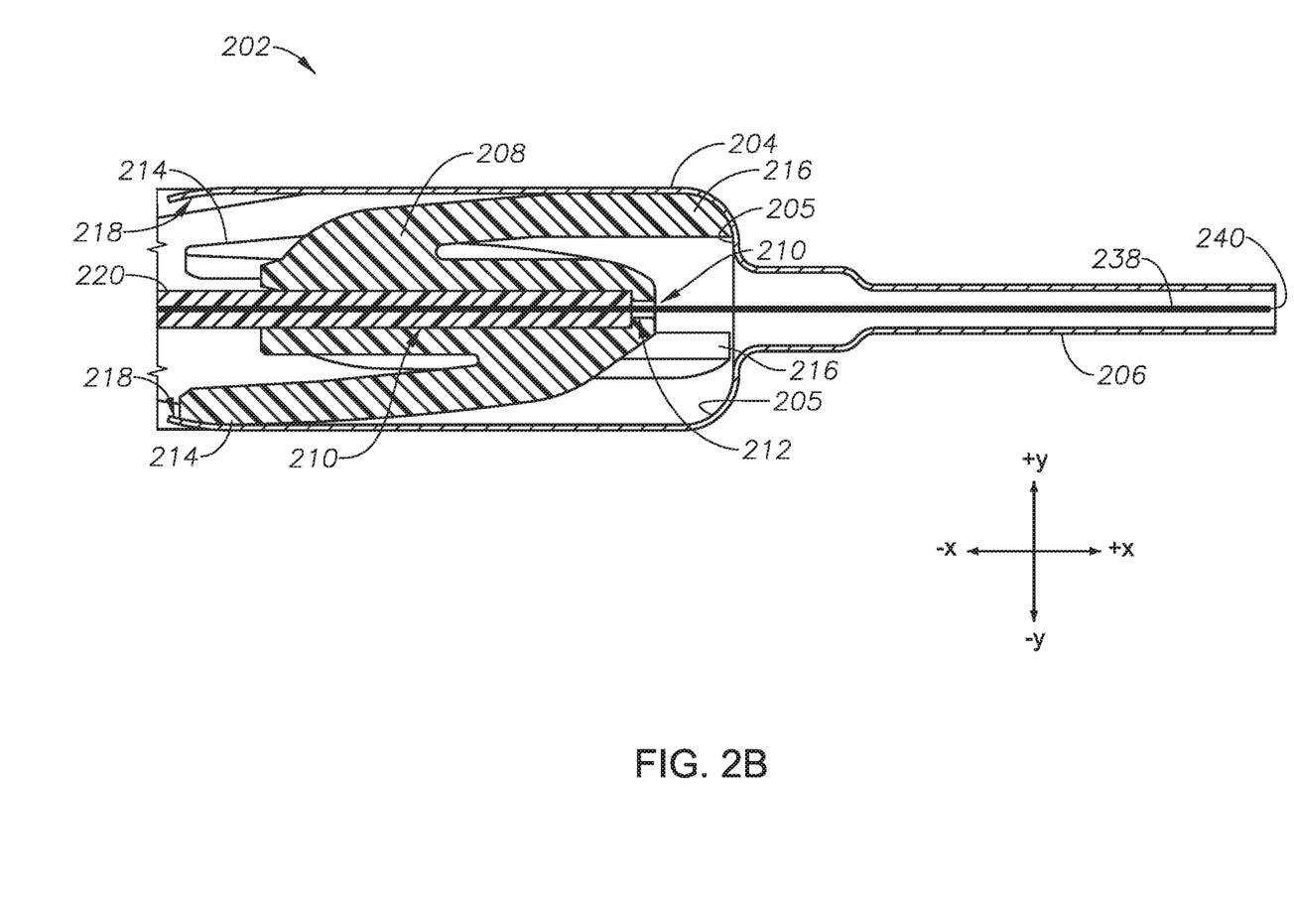
FIG. 2B illustrates a positioning insert of an optical fiber support assembly housed within a cannula.

FIGS. 2A-2D illustrate features of an optical fiber support assembly 219 according to some embodiments of the present technology. FIG. 2A illustrates the optical fiber support assembly 219 including an optical fiber support tube 220 with a distal end inserted in a passage 210 of a positioning insert 208. Also, as shown in FIG. 2B, the positioning insert 208 is configured to fit within a cannula 202. The optical fiber support tube 220 can provide structural integrity to an optical fiber 238 contained therein, thereby allowing the use of a thin optical fiber 238 (e.g. eighty microns diameter or less). A thin optical fiber 238 reduces interference with the delivery of infusion fluid through an infusion fluid outlet tube and the cannula 202. The optical fiber support assembly 219 includes the attachment tube 236 for coupling with an optical fiber illumination assembly (described in greater detail below).

The cannula 202 can include a flared proximal body 204 and a thin distal tip 206. The positioning insert 208 can have arms 214, 216 and can be configured to fit tightly within the flared proximal body 204. Also, the flared proximal body 204 of the cannula 202 has a base 205 that resists axial motion (in the +X direction) of the arms 216 of the positioning insert 208.

Figure 2C:
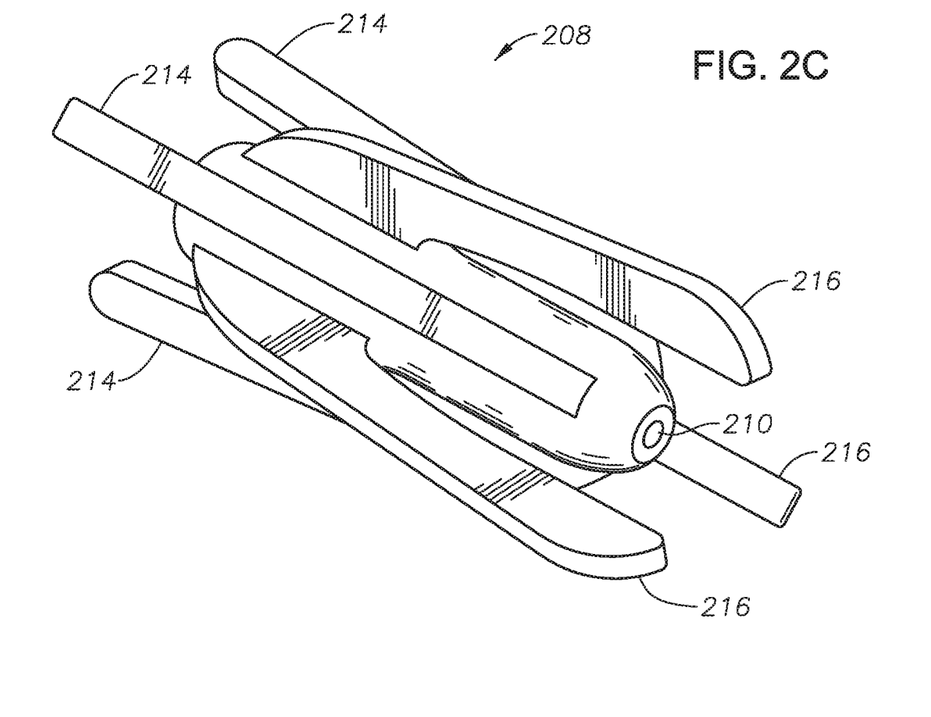
FIG. 2C illustrates a positioning insert of an optical fiber support assembly.

The configuration of the positioning insert 208, along with arms 214, 216, can be selected to allow a substantially laminar and minimally-restricted fluid flow over the positioning insert 208 while in the cannula 202. A configuration of the positioning insert 208 that achieves this goal is shown in FIG. 2C. As shown in FIG. 2C, the positioning insert 208 includes two sets of three arms 214, 216 protruding from the positioning insert 208. The arms 214, 216 are specifically shaped to interface with an inner surface 218 of the flared proximal body 204 of the cannula 208. Also, the two sets of arms 214, 216 have respective attachment points on opposing ends of the axial length of the positioning insert 208, i.e. dual-opposing cantilevered arms. The two sets of arms 214, 216 can be interleaved and can extend away from the respective attachment points and towards the opposing side of the axial length of the positioning insert 208. The two sets of arms 214, 214 can also be equally radially spaced, e.g. 60° apart. Additionally, the arms 214, 216 can have terminal ends with a curved profile that match a curved profile of the base 205 of the cannula 202. Further, the arms 214, 216 can be made from an elastic material and can deflect when inserted into the cannula 202 to provide a resisting force. The arrangement of two sets of interleaved, dual-opposing cantilevered, elastic arms 214, 216 allows the arms to flex substantially radially in contact with the inner surface 218 of the cannula 202. This enables a snap-fit assembly without other means of attachment, and provides a self-retaining, compliant fit of the positioning insert 208 within the flared proximal bod portion 204 of the cannula 202. Although specific configurations of the positioning insert 208 are described with reference to FIGS. 2A-2D, those with ordinary skill in the art having the benefit of the disclosure will readily appreciate that a wide variety of configurations for positioning inserts can be used to achieve the utility of the present technology.

Referring again to FIG. 2B, the positioning insert 208 also includes a passage 210 for holding the optical fiber support tube 220 within the flow path of infusion fluid in an infusion fluid outlet tube 222. The positioning insert 208 also positions an optical fiber 238 within a thin distal tip 206 of the cannula 202. The passage 210 can also include a decreased diameter portion 212 that resists the motion of the optical fiber support tube 220 (in the +x direction), but which allows the optical fiber 238 to traverse therethrough. In some cases, the decreased diameter portion 212 is further used to accommodate adhesive without the adhesive spilling into the flow path and interfering with the flow of infusion fluid.

Although the positioning insert 208 shown in FIGS. 2A-2D positions the optical fiber support tube 220 and the optical fiber 238 in a center- or substantially center-position within the cannula 202 and infusion fluid outlet tube 222, a wide variety of other positions can equally be achieved with alternative embodiments of the positioning insert. Accordingly, as used herein, the terms "center," "centers," "substantially centers," "centered," "substantially centered," "centration," and "substantial centration" are not intended to limit the disclosure to any particular embodiments. For example, in some cases, a positioning insert can position the optical fiber support tube 220 and the optical fiber 238 along a wall of the infusion fluid outlet tube 222.

In some cases, a distal fiber tip 240 of the optical fiber 238 extends short of the terminal end of the thin distal tip 206 of the cannula 202 to leave a small space between the end of the optical fiber 238 and thin distal tip 206 of cannula 208. The small space can protect the optical fiber 238 (e.g. when inserted into a hubbed entry cannula) and still allow light from the optical fiber 238 to spread out in a wide field.

Also, an extent that the light from the optical fiber 238 spreads is a function of a material selected for the optical fiber 238 and the numerical aperture of the beam exiting the optical fiber 238. Therefore, in some cases, the small space between the distal fiber tip 240 and the terminal end of the thin distal tip 206 of the cannula 202 is selected based on the material selected for the optical fiber 238 and a desired amount of spread.

Likewise, since the base 205 of the flared of the flared proximal body 204 resists axial motion (in the +X direction) of the arms 216 of the positioning insert 208, the small space between the distal fiber tip 240 and the terminal end of the thin distal tip 206 of the cannula 202 can be related to the dimensions of the arms 216 (when the arms 216 contact the base 205 and the terminal end of the optical fiber support tube 220 is in contact with the decreased diameter portion 212 of the passage). Accordingly, the size of the small space can be specified by selecting (e.g. during assembly, as explained below) a length that the optical fiber 238 that extends past the optical fiber support tube 220 and past the arms 216.

Figure 2D:
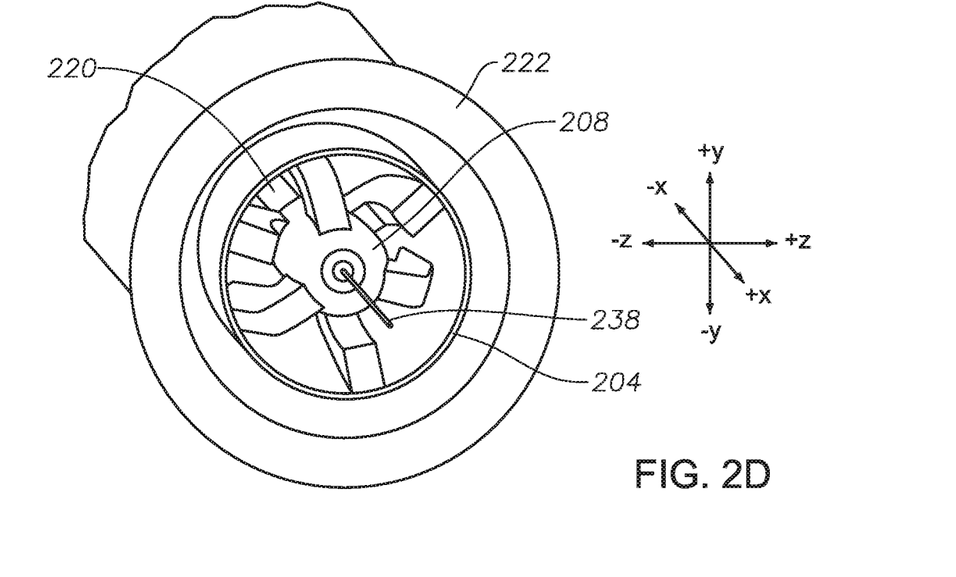
FIG. 2D illustrates a cut-away view of a positioning insert fit within a flared proximal body of a cannula and within an infusion fluid outlet tube.

FIG. 2D illustrates a cut-away view of the positioning insert 208 fit within the flared proximal body 204 of a cannula 202. As shown, the positioning insert 208 substantially centers the optical fiber support tube 220 and the optical fiber 238 within the cannula 202 and an infusion fluid outlet tube 222.

As described in greater detail below, a length of the optical fiber support tube 220 can be selected based on a length of the infusion fluid outlet tube and the dimensions of a Y-shaped fitting used in an ophthalmic surgical assembly. Also, a material for the optical fiber support tube 220 can be selected for mechanical stability and biocompatibility, e.g. a biocompatible polyetheretherketone material.

Figure 3:
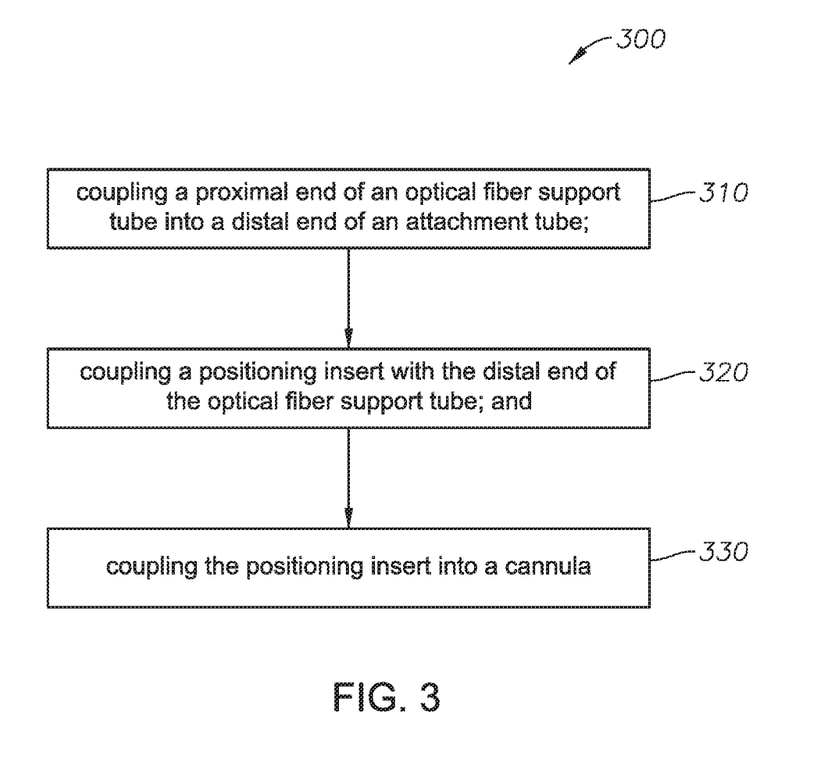
FIG. 3 illustrates a method of assembling an optical fiber support assembly.

FIG. 3 illustrates a method 300 of assembling an optical fiber support assembly according to some embodiments of the present technology. The method 300 can involve coupling a proximal end of an optical fiber support tube into the distal end of an attachment tube 310. As explained in greater detail below, the attachment tube can be used to attach the optical fiber support assembly with other components of an illuminated infusion cannula system, e.g. a Y-shaped fitting. Next, the method 300 involves coupling a positioning insert with the distal end of the optical fiber support tube 320. In some cases, coupling a positioning insert with the distal end of the optical fiber support tube can involve fully inserting the optical fiber support tube into the passage of the positioning insert until the optical fiber support tube hits a decreased diameter portion of the passage. The method 300 can also involve coupling the positioning insert into a cannula 330.

Figure 4:
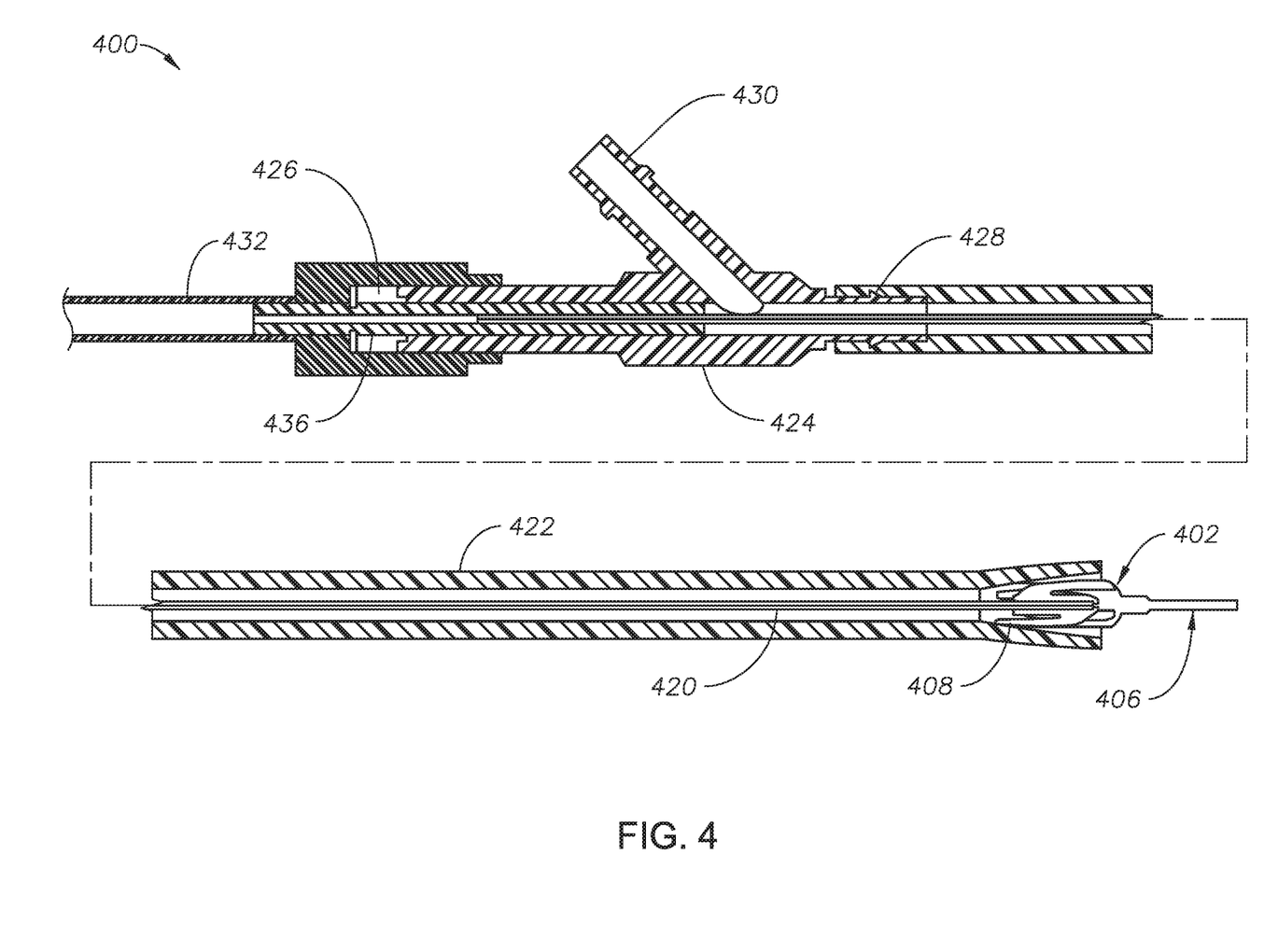
FIG. 4 illustrates an optical fiber support assembly integrated into an illuminated infusion surgical assembly.

FIG. 4 illustrates an optical fiber support assembly integrated into an illuminated infusion surgical assembly 400. The illuminated infusion surgical assembly 400 includes an optical fiber support tube 420 coupled with an attachment tube 436 and a positioning insert 408. The positioning insert 408 is coupled with a cannula 402 and the attachment tube 436 is slide into a Y-shaped fitting 424 and coupled with an optical fiber illumination assembly 432 at a first attachment point 426 of the Y-shaped fitting 424. The optical fiber illumination assembly 432 includes an optical fiber (not shown) extending through the attachment tube 436, into the optical fiber support tube 420, through the Y-shaped fitting 424, through the length of the optical fiber support tube 420, through the passage (not labeled) of the positioning insert 408 and into the thin distal tip 406 of the cannula 402. The cannula 402 is coupled with a distal end of an infusion fluid outlet tube 422 and the proximal end of an infusion fluid outlet tube 422 is coupled with a second attachment point 428 of the Y-shaped fitting 424. A third attachment point 430 of the Y-shaped fitting 424 can couple with an infusion fluid inlet tube (not shown). The illuminated infusion surgical assembly 400 shown in FIG. 4 can be used to simultaneously deliver illumination through the optical fiber and infusion fluid through the infusion fluid inlet tube and infusion fluid outlet tube 422. As explained above, the size of the optical fiber, the size of the optical fiber support tube 420, the shape of the positioning insert, and their relative configurations can support simultaneous illumination and infusion with a substantially laminar and minimally-restricted fluid flow and a wide beam of illumination without shadows.

Figure 5:
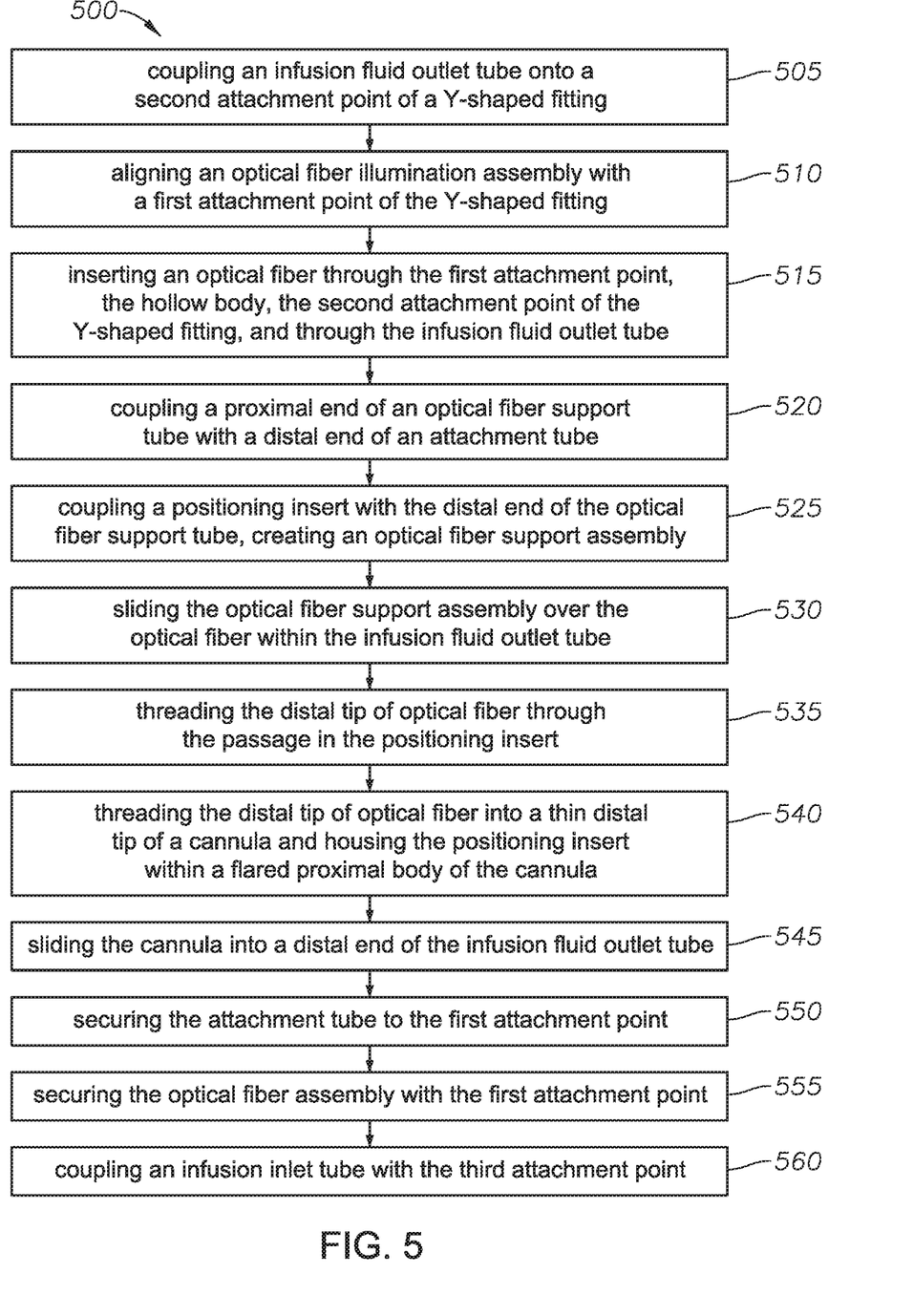
FIG. 5 illustrates a method of assembling an illumination infusion surgical assembly.

FIG. 5 illustrates a method 500 of assembling an illumination infusion surgical assembly according to some embodiments of the present technology. FIGS. 6A-6F illustrate the various steps of method 500. The method 500 of assembling an illumination infusion surgical assembly involves coupling an infusion fluid outlet tube onto a second attachment point of a Y-shaped fitting 505, aligning an optical fiber illumination assembly with a first attachment point of the Y-shaped fitting 510, and inserting an optical fiber through the first attachment point, the hollow body, the second attachment point of the Y-shaped fitting, and through the infusion fluid outlet tube 515.

Figure 6A:
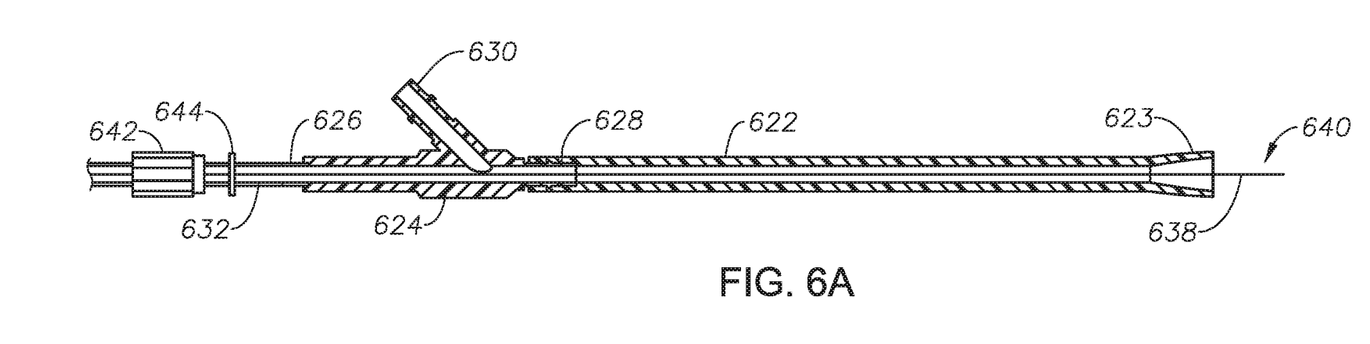
FIG. 6A illustrates an optical fiber illumination assembly aligned with a Y-shaped fitting coupled with an infusion fluid outlet tube.

FIG. 6A illustrates an optical fiber illumination assembly 632 aligned with a Y-shaped fitting 624 coupled with an infusion fluid outlet tube 622. The Y-shaped fitting 624 has a substantially hollow body, a first attachment point 626, a second attachment point 628, and a third attachment point 630. An optical fiber illumination assembly 632 is aligned with the first attachment point 626 and an infusion fluid outlet tube 622 is coupled to the second attachment point 628. The optical fiber illumination assembly 632 also includes a nut 642 and a washer 644 which are later used to couple the optical fiber illumination assembly 632 to the first attachment point 626. Also shown in FIG. 6A, the optical fiber 638 from the optical fiber illumination assembly 632 is inserted through the first attachment point, the hollow body of the Y-shaped fitting 624, the second attachment point 628, and through the infusion fluid outlet tube 622. A distal fiber tip 640 of the optical fiber 638 extends past a distal end 623 of the infusion fluid outlet tube 622.

Figure 6B:
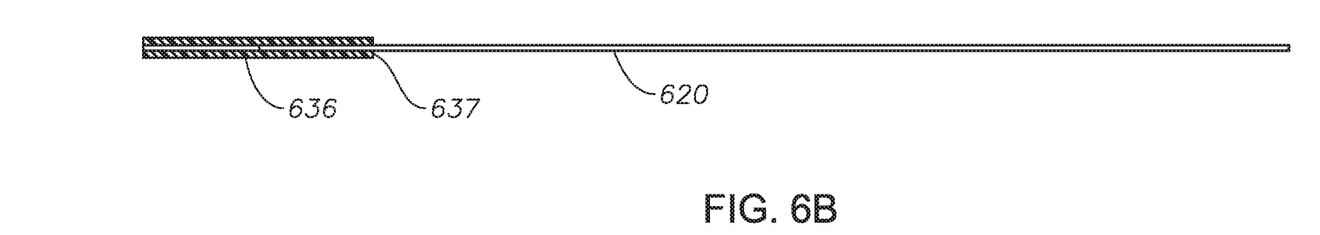
FIG. 6B illustrates the optical fiber support tube coupled with the attachment tube.

The method 500 further involves coupling a proximal end of an optical fiber support tube with a distal end of an attachment tube 520. FIG. 6B illustrates an optical fiber support tube 620 coupled with the attachment tube 636. In some cases, the optical fiber support tube 620 is coupled with the attachment tube 636 using a curable-adhesive at joint 637. A material for the optical fiber and a length of a portion of the optical fiber support tube 620 that extends out of the attachment tube 636 can be selected to extend through a positioning insert (not shown) into a distal tip of a cannula (not shown) to a point short of the terminal end of the distal tip of the cannula, such that light emitted by the distal fiber tip of the optical fiber is protected and can spread in a cone through the distal tip of the cannula. For example, in some cases, the length of a portion of the optical fiber support tube 620 that extends out of the attachment tube 636 can be ninety-one millimeter plus or minus one millimeter.

Figure 6C:
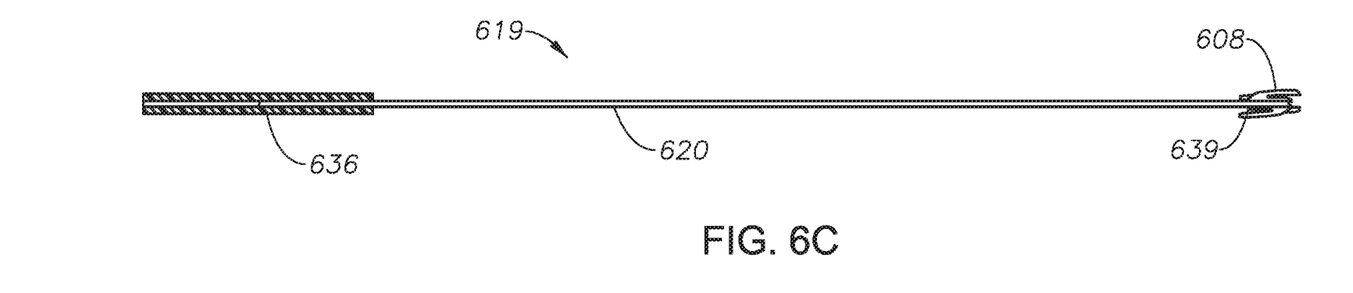
FIG. 6C illustrates an optical fiber support assembly including an attachment tube, an optical fiber support tube, and a positioning insert.

Next, the method 500 involves coupling a positioning insert with the distal end of the optical fiber support tube 525, creating an optical fiber support assembly 619. FIG. 6C illustrates an optical fiber support assembly 619 including an attachment tube 636, an optical fiber support tube 620, and a positioning insert 608. The optical fiber support tube 620 can be coupled with the positioning insert 608 using a curable adhesive at joint 639.

Figure 6D:
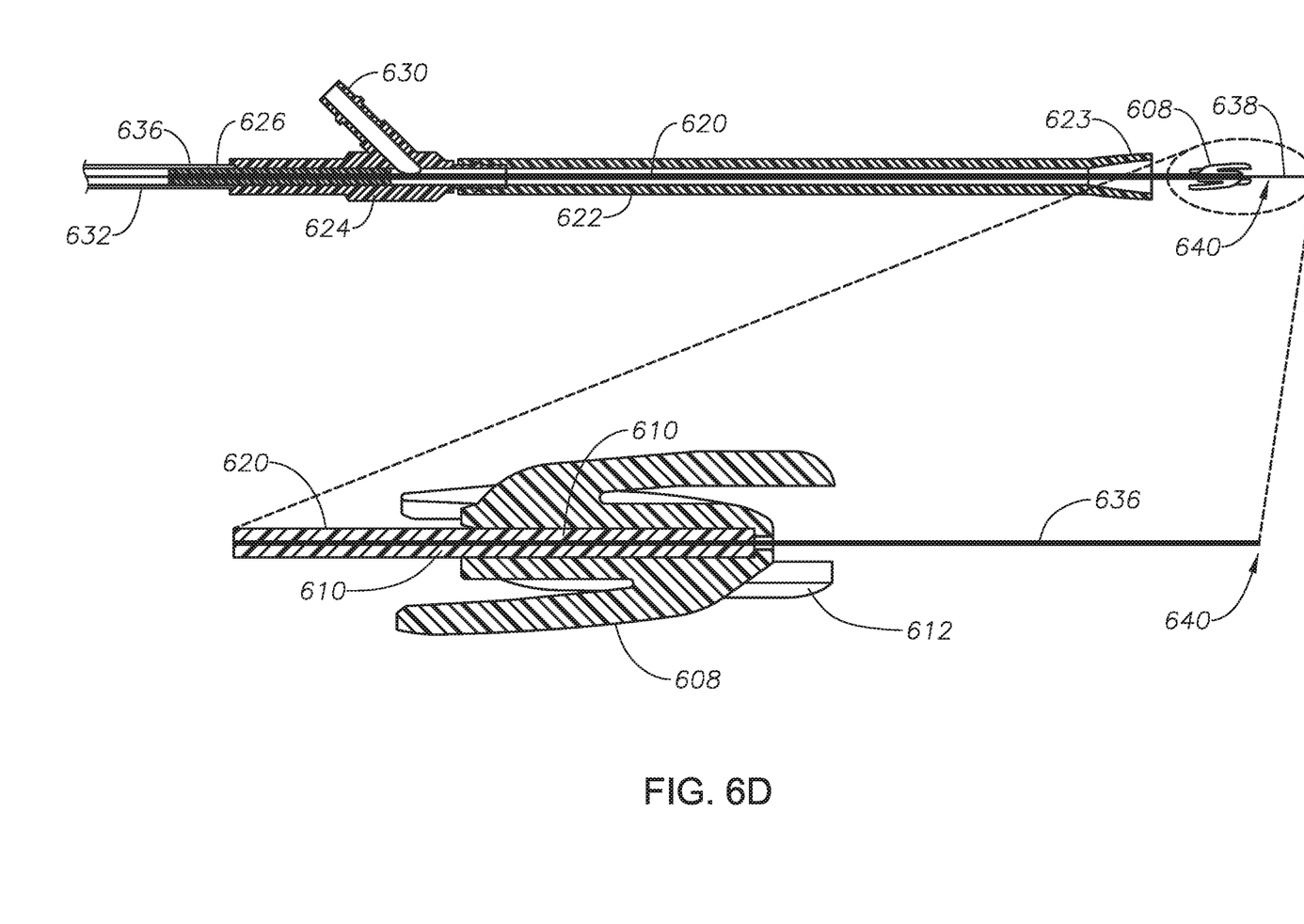
FIG. 6D illustrates an attachment tube slid through a Y-shaped fitting and an optical fiber support tube positioned within an infusion fluid outlet tube.

The method 500 further involves sliding the optical fiber support assembly over the optical fiber within the infusion fluid outlet tube 530 further involving: sliding the attachment tube into the infusion fluid outlet tube; threading the optical fiber through the attachment tube and optical fiber support tube; sliding the attachment tube through the second attachment point, through the hollow body, through the first attachment point, and aligning the attachment tube with the optical fiber illumination assembly; and threading the distal tip of optical fiber through the passage in the positioning insert 535. FIG. 6D illustrates the attachment tube 636 slid through the Y-shaped fitting 624 past the first attachment point 626 and the optical fiber support tube 620 positioned within the infusion fluid outlet tube 622. The optical fiber 638 is thread through the passage 610 of the positioning insert 608 with the distal fiber tip 640 of the optical fiber 638 extending past the positioning insert 608, e.g. 5.1 millimeters+/−0.1 millimeter. Also, the optical fiber support tube 620 is coupled within the passage 610 of the positioning insert 608 with the decreased diameter portion 612 of the passage 610 resisting further axial motion of the optical fiber support tube 620.

Next, the method 500 involves threading the distal tip of optical fiber into a thin distal tip of a cannula and housing the positioning insert within a flared proximal body of the cannula 540 and sliding the cannula into a distal end of the infusion fluid outlet tube 545, thereby further sliding the attachment tube through the first attachment point of the Y-shaped fitting.

Figure 6E:
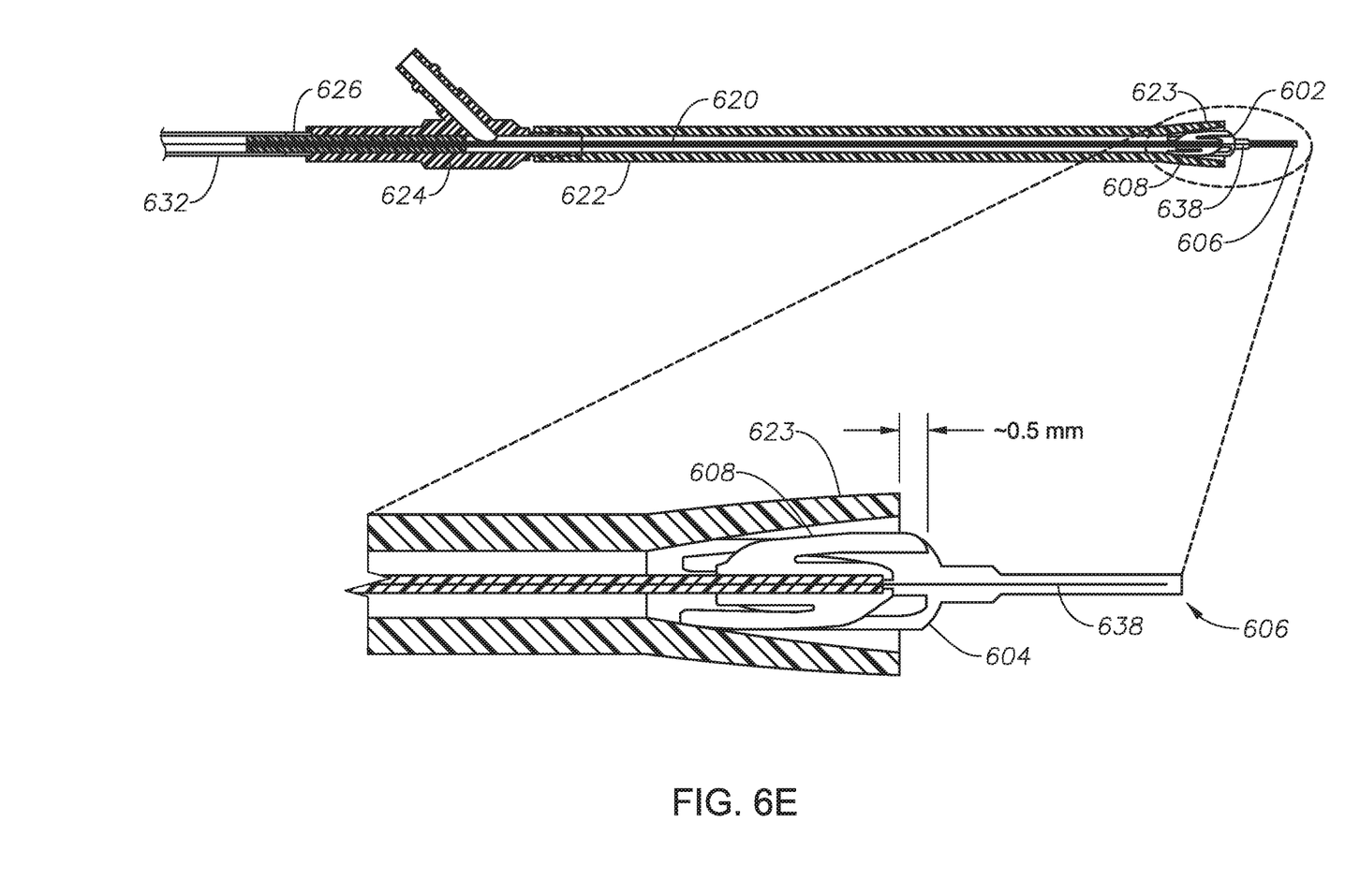
FIG. 6E illustrates an optical fiber thread into the thin distal tip of a cannula and a positioning insert housed within a flared proximal body of the cannula.

FIG. 6E illustrates the optical fiber 638 thread into the thin distal tip 606 of a cannula 602 and the positioning insert 608 housed within the flared proximal body 604 of the cannula 602. The cannula 602 is coupled within the distal end 623 of the infusion fluid outlet tube 622, causing the optical fiber support tube 620 to slide further towards the optical fiber illumination assembly 632 through the infusion fluid outlet tube 622 and the Y-shaped fitting 624. Also, attachment tube 636 is slid further through the Y-shaped fitting 624 and further past the first attachment point 626 and engaged with the optical fiber illumination assembly 632.

The method 500 further involves securing the attachment tube to the first attachment point 550 of the Y-shaped fitting. For example, a curable adhesive can be applied to couple the attachment tube to the first attachment point. Next, the method 500 involves securing the optical fiber assembly with the first attachment point 555. For example, the first attachment point can having external threading and the washer 644 and nut 642 can be tightened over the external threading. Finally, the method 500 can involve coupling an infusion fluid inlet tube with the third attachment point of the Y-shaped fitting 560.

Figure 6F:
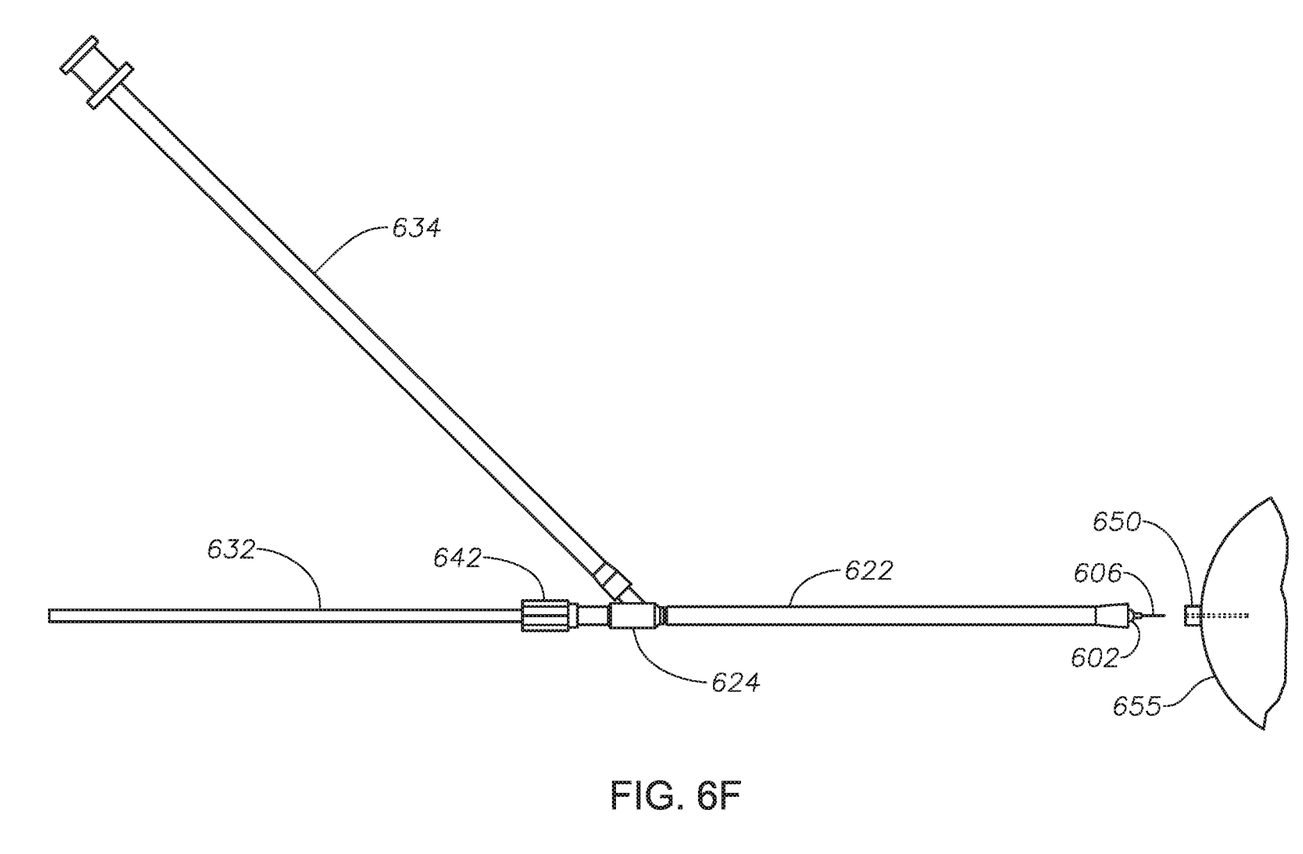
FIG. 6F illustrates an illuminated infusion surgical assembly with a cannula configured to deliver illumination and infusion fluid to an eye through a hubbed entry cannula.

FIG. 6F illustrates the illuminated infusion surgical assembly 600 with an attachment tube (not shown) of an optical fiber support assembly (not shown) secured to an optical fiber illumination assembly 632. The optical fiber illumination assembly 632 is coupled with the Y-shaped fitting 624 with the nut 642. The optical fiber support assembly and the optical fiber (not shown) are positioned within the cannula 602 through the infusion fluid outlet tube 622 and via the positioning inset (not shown). Also, an infusion fluid inlet tube 634 is coupled with the third attachment point 630 of the Y-shaped fitting 624.

The illuminated infusion surgical assembly 600 illustrated in FIG. 6F is configured to deliver illumination from the optical fiber illumination assembly 632 through the optical fiber to the thin distal tip 606 of the cannula 602. As explained above, the dimensions of the optical fiber support assembly and the optical fiber can be selected such that the distal fiber tip of the optical fiber is positioned short of the terminal end of the thin distal tip 606 of the cannula 602 such that light emitted by the distal fiber tip can spread in a cone through the thin distal tip 606 of the cannula 602 without the optical fiber extending past the terminal end of the thin distal tip 606 of the cannula 602, thereby protecting the integrity of the optical fiber when inserted through a hubbed entry cannula 650 inserted into an eye 655.

Also, infusion fluid from the infusion fluid inlet tube 634 can be delivered through the infusion fluid outlet tube 622, through the infusion fluid outlet tube 622, and to the cannula 602. As described above, the optical fiber support assembly is configured with a very thin optical fiber, a thin optical wire support tube, and an armed positioning insert such that the infusion fluid flows in a substantially laminar regime with minimal restriction.

Accordingly, the illuminated infusion surgical assembly 600 supports combined illumination and infusion fluid delivery to the eye 655 without unacceptably affecting infusion fluid flow characteristics or illumination quality while also protecting the optical fiber during insertion through the hubbed entry cannula 650.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An ophthalmic surgery assembly comprising:
    a cannula having a thin distal tip and a flared proximal body;
    a positioning insert having a shape configured to fit tightly within the flared proximal body of the cannula and having a passage disposed through an axial length of the positioning insert; and
    an optical fiber support tube having an inner diameter configured to allow an optical fiber to be housed therein and having an outer diameter configured to fit into the passage in the positioning insert such that the positioning insert, when placed within the flared proximal body of the cannula, maintains substantial centration of a distal fiber tip of the optical fiber;
    wherein the positioning insert is configured with two sets of arms protruding from the positioning insert, the two sets of arms each configured to contact an inner surface of the flared proximal body of the cannula;
    wherein the two sets of arms have respective attachment points on opposing ends of the axial length of the positioning insert, and wherein the two sets of arms extend away from the respective attachment points and towards an opposing side of the axial length of the positioning insert.

2. The ophthalmic surgery assembly of claim 1, further comprising:
    an optical fiber illumination assembly including the optical fiber to be housed in the optical fiber support tube;
    an infusion fluid outlet tube with a proximal end and a distal end configured to secure the cannula therein; and
    a Y-shaped fitting having a hollow body, a first attachment point for coupling with the optical fiber illumination assembly, a second attachment point for coupling with the infusion fluid outlet tube, and a third attachment point for coupling with an infusion fluid inlet tube.

3. The ophthalmic surgery assembly of claim 2, wherein the distal end of the infusion outlet tube is elastic and provides a retaining force on an outer surface of the flared portion of the cannula when the cannula is housed therein.

4. The ophthalmic surgery assembly of claim 2, wherein the distal end of the infusion outlet tube is flared.

5. The ophthalmic surgery assembly of claim 2, further comprising:
    an attachment tube having an inner diameter configured for housing a proximal portion of the optical fiber support tube and having an outer diameter configured to:
    traverse an opening in the second attachment point, the hollow body, and an opening in the first attachment point; and
    couple with an outside portion of the opening in the first attachment point.

6. The ophthalmic surgery assembly of claim 5, wherein a length of the attachment tube, a length of the optical fiber support tube, and a length of the optical fiber are selected such that:
    when the optical fiber is housed in the optical fiber support tube,
    when the proximal portion of the optical fiber support tube is housed within the attachment tube, and
    when the attachment tube is coupled to the first attachment point if the Y-shaped fitting, a portion of the optical fiber including the distal fiber tip extends past the length of the optical fiber support tube.

7. The ophthalmic surgery assembly of claim 6, wherein the passage in the positioning insert has a decreased diameter portion in a distal end of the passage, wherein the decreased diameter portion has a diameter configured to resist axial motion of the optical fiber support tube and to allow passage of the portion of the optical fiber including the distal fiber tip that extends past the length of the optical fiber support tube.

8. The ophthalmic surgery assembly of claim 7, wherein the length of the portion of the optical fiber including the distal fiber tip that extends past the length of the optical fiber support tube is selected to extend into the distal tip of the cannula to a point short of a terminal end of the distal tip of the cannula and where light emitted by the distal fiber tip can spread in a cone projecting substantially from an interior of the distal tip of the cannula.

9. The ophthalmic surgery assembly of claim 1, wherein the optical fiber has an outside diameter less than or equal to eighty microns.

10. The ophthalmic surgery assembly of claim 2, further comprising:
the infusion fluid inlet tube configured to couple with the third attachment point of the Y-shaped fitting and deliver infusion fluid through the hollow body of the Y-shaped fitting, over an attachment tube, over the optical fiber support tube, over the positioning insert in the cannula, and out of the thin distal tip of the cannula.

11. The ophthalmic surgery assembly of claim 1, wherein each of the two set of arms contain three arms.

12. The ophthalmic surgery assembly of claim 1, wherein the two sets of arms are interleaved.

13. The ophthalmic surgery assembly of claim 1, wherein the arms are flexible.

14. The ophthalmic surgery assembly of claim 1, wherein a profile of the two sets of arms is selected to allow an infusion fluid to flow through the cannula according to a substantially laminar flow regime.

15. A method of assembling an illuminated infusion cannula comprising:
coupling an infusion fluid outlet tube onto a Y-shaped fitting having a hollow body, a first attachment point for coupling with an optical fiber illumination assembly, a second attachment point for coupling with the infusion fluid outlet tube, and a third attachment point for coupling with an infusion fluid inlet tube, wherein the first attachment point and the second attachment point are configured substantially coaxially;
aligning an optical fiber illumination assembly with the first attachment point;
inserting an optical fiber of the optical fiber illumination assembly through the first attachment point, the hollow body, the second attachment point, and the infusion fluid outlet tube;
coupling a proximal end of an optical fiber support tube with a distal end of an attachment tube;
coupling a positioning insert with the distal end of the optical fiber support tube, the positioning insert having a shape configured to fit tightly within the flared proximal body of a cannula and having a passage disposed through an axial length of the positioning insert;
inserting the optical fiber into the attachment tube;
sliding the attachment tube around the optical fiber, into the infusion fluid outlet tube, through the second attachment point, through the hollow body, through the first attachment point, and into the optical fiber illumination assembly, wherein sliding the attachment tube further involves: pulling the optical fiber support tube over the optical fiber and through the infusion fluid outlet tube towards the first attachment point, and threading a distal tip of the optical fiber through the passage disposed through an axial length of the positioning insert;
threading the distal tip of the optical fiber into a thin distal tip of a cannula and housing the positioning insert within a flared proximal body of the cannula;
sliding the cannula into a distal end of the infusion fluid outlet tube, thereby further sliding the optical fiber support tube towards the first attachment point and the attachment tube through the first attachment point;
securing the attachment tube to the first attachment point; and
securing the optical fiber assembly with the first attachment point;
wherein the positioning insert is configured to tightly fit within the flared proximal body of the cannula and maintain substantial centration of the distal fiber tip of the optical fiber, wherein the positioning insert in configured with two sets of arms protruding from the positioning insert, the two sets of arms each configured to contact an inner surface of the flared proximal body of the cannula, wherein each of the two set of arms contain three arms, wherein the two sets of arms have respective attachment points on opposing ends of the axial length of the positioning insert, and wherein the two sets of arms extend away from the respective attachment points and towards an opposing side of the axial length of the positioning insert, wherein the two sets of arms are interleaved.

16. The method of assembling an illuminated infusion cannula of claim 15, further comprising:
selecting a length of the attachment tube, a length of the optical fiber support tube, and a length of the optical fiber such that: when the optical fiber is housed in the optical fiber support tube, when the proximal portion of the optical fiber support tube is housed within the attachment tube, and when the attachment tube is coupled to the first attachment point if the Y-shaped fitting, a portion of the optical fiber including the distal fiber tip extends past the length of the optical fiber support tube.

17. The method of assembling an illuminated infusion cannula of claim 15, further comprising:
coupling the infusion fluid inlet tube with the third attachment point; and
delivering infusion fluid through the hollow body of the Y-shaped fitting, over the attachment tube, over the optical fiber support tube, over the positioning insert in the cannula, and out of the thin distal tip of the cannula.

* * * * *